United States Patent [19]
Henning

[11] Patent Number: 5,960,139
[45] Date of Patent: Sep. 28, 1999

[54] COUPLING DEVICE FOR A LIGHT GUIDE

[75] Inventor: Wolfram Henning, Traubenstrasse 15, D-90584 Allersberg, Germany

[73] Assignee: Wolfram Henning

[21] Appl. No.: 08/850,925

[22] Filed: May 2, 1997

[51] Int. Cl.[6] .................................................. G02B 6/36
[52] U.S. Cl. ........................... 385/78; 385/72; 385/73; 385/60
[58] Field of Search ............................ 385/78, 72, 73, 385/76, 60, 59, 77, 88, 80, 139, 141

[56] References Cited

U.S. PATENT DOCUMENTS 5,764,834   6/1998   Hultermans ........................... 385/78 X

FOREIGN PATENT DOCUMENTS 44 42 347 A1   of 1996   Germany .

*Primary Examiner*—Phan T. H. Palmer
*Attorney, Agent, or Firm*—Evenson, McKeown, Edwards & Lenahan, P.L.L.C.

[57] ABSTRACT

In an arrangement for coupling an optical waveguide to an optical device, particularly for a laser application, or to another optical waveguide, the optical waveguide is held in a fiber plug which can be connected with a countercoupling part in which the end of the waveguide is introduced into a fixed centering sleeve and centered. The discardable fiber plug of simple construction is fastened on the elastic fiber cladding of the optical waveguide, and the projecting front end of the waveguide is bared down to the optical fiber cladding. The optical waveguide fiber which is introduced into said centering sleeve is bared, and centering is facilitated by the elasticity of the fiber. The centering sleeve may be provided with an introducing cone, and may have an elastic diameter, and the fiber plug may be fastened on the countercoupling part by means of instant plug-in connections.

7 Claims, 2 Drawing Sheets

COUPLING DEVICE FOR A LIGHT GUIDE

BACKGROUND AND SUMMARY OF THE INVENTION

The invention relates to an arrangement for coupling optical waveguides to an optical device, particularly for a laser application, the optical waveguide being held in a fiber plug which can be connected with a countercoupling part of the optical device and being bared on its end which is to be introduced into the countercoupling part, and having a centering unit for the optical waveguide.

When coupling laser beams into optical waveguides—and correspondingly for connecting two optical waveguides—it is important align the optical axes of the optical waveguide and of the laser beam. Deviations from center positions result in power losses and, in the case of higher laser powers, may even lead to the destruction of the optical waveguide. In the case of the known couplings and plug-type connections for optical waveguides, the deviation of the alignment of the optical waveguide with respect to the given optical axis of the laser beam or of another optical waveguide is influenced by a plurality of mechanical tolerances at the plug-type connectors, such as the inside diameter of the coupling sleeve, the outside diameter of the plug, the inside diameter and the conical form of the plug bore, the outside diameter and the concentricity of the optical waveguides, and the like. The low permissible mechanical tolerances for optical waveguide plugs are important factors for the manufacturing methods and the relatively high prices of the previous coupling arrangements.

German Patent Document DE 42 01 769 C1 describes a coupling arrangement of initially mentioned type in which the centering unit is constructed such that the centering sleeve is on the fiber plug itself. When this fiber plug is now introduced into the optical device and "centered", only an extremely poor centering can be achieved in this case because of the different given tolerances. These tolerances may exist between the outside diameter of the plug pin and of the plug socket, the inside diameter and the outside diameter of the plug pin, between the plug pin and the shown supporting body, between the bore in the supporting body and the fiber passing through and may consist of concentricity tolerances of the bore in the supporting body. The cumulative effect of these tolerances no longer permits a precise adjustment which has the result that only an insufficient coupling-in is achieved. In an extreme case, the laser spot may even be focused beside to the fiber.

It is therefore an object of the invention to construct a coupling arrangement for optical waveguides, particularly for the coupling to laser systems, such that it can be manufactured at low cost and nevertheless with a very high coupling quality so that, predominantly in the medical field, it is suitable to be used as a throw-away plug, which is absolutely required, for example, for body probes, which may not be used more than once.

For achieving this object, it is provided according to the invention that the centering unit is arranged in the countercoupling part and comprises a centering sleeve which is aligned flush with respect to the optical axis of the adjoining optical device. The centering unit is fixedly connected with the countercoupling part, and when the fiber plug is plugged into the countercoupling part, the fiber is introduced into the centering sleeve in which it is centered.

The invention takes into account the fact that only the plug with the connecting optical waveguide is required to be discarded whereas, with respect to the countercoupling part which establishes the connection either to another optical waveguide (which must not be discarded) or to the laser system of a medical instrument, it is not important that an optically precise alignment with the centering unit is carried out here at high expenditures. The mechanical tolerances are reduced to those of the optical waveguide bore in the plug-in socket and the diameter as well as the concentricity of the fiber. All other tolerances, as those mentioned above, play no role for the optical alignment; that is, the tolerances with which the plug is held in the coupling part do not cumulate to the tolerances to be minimized with ordinary expenditures which exist between the diameter of the optical waveguide bore of the centering sleeve and the diameter as well as the concentricity of the optical waveguide fiber.

According to another embodiment of the invention, the only existing tolerance which becomes noticeable as an alignment error can be reduced by providing a centering sleeve which is elastic in its diameter, and is, for example, slotted or constructed of an inherently elastic material. As a result, the mentioned tolerance can virtually be reduced to zero.

The compensation between the tolerances existing between the fiber plug and the countercoupling part, which according to the invention need not specifically be taken into account, is obtained by the elastic bendability of the fiber of the optical waveguide which projects toward the front over the plug. For introducing this fiber into the centering sleeve, the latter is preferably provided with an introducing cone. The end to be introduced into the countercoupling part of the optical waveguide can be bared down to the optical fiber cladding.

As demonstrated, the coupling arrangement according to the invention can also be used for connecting two optical waveguides, in which case a countercoupling part equipped with two plug receiving devices situated and aligned opposite one another and with a centering unit is used for receiving their two optical waveguide fibers.

The fiber plugs can be fastened on the countercoupling part by means of instant plug-in connection. All kinds of different instant plug-in connections are suitable for this purpose which have already been developed for electric plug-type connections, for example, plug-type connections having a ball-type latch and an outer spring-loaded screw cap, as frequently used, for example, during the quick-action chucking of drills.

The optical waveguide can be connected with the fiber plug with low precision requirements by means of shrinking-on, chucking, gluing or injection molding on the elastic fiber cladding of the optical waveguide. As a result, the costs for producing such optical waveguides with the fiber plug as a disposable article can be minimized.

In this case, it is naturally still within the scope of the invention to provide the fiber projecting out of the front side of the fiber plug, in a required length, by means of optical processing or breaking, with the required light entry surface.

Other objects, advantages and novel features of the present invention will become apparent from the following detailed description of the invention when considered in conjunction with the accompanying drawings.

DETAILED DESCRIPTION OF THE DRAWINGS

Figure 1:
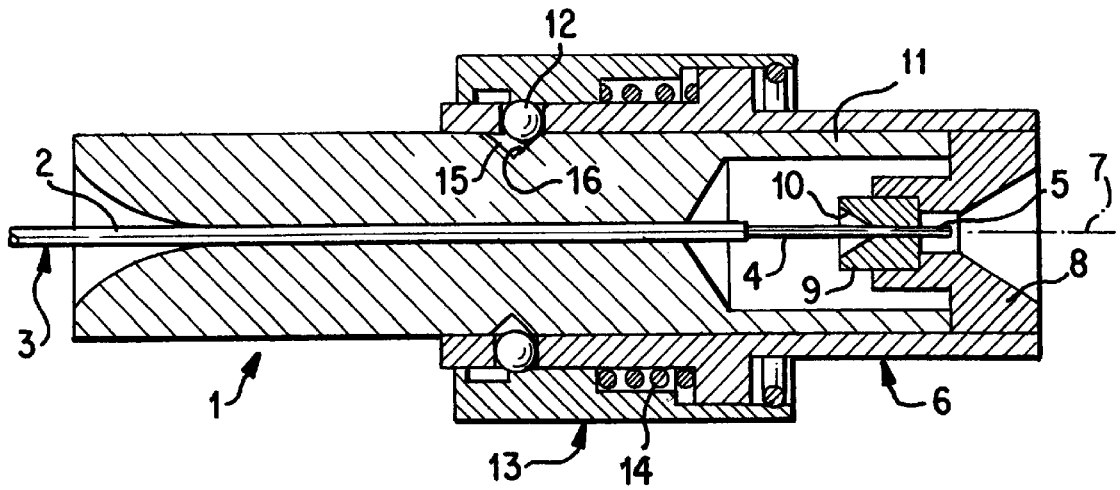
FIG. 1 is an enlarged sectional view of a coupling arrangement for connecting a fiber plug with the output jack of a laser in the latched position.
Figure 2:
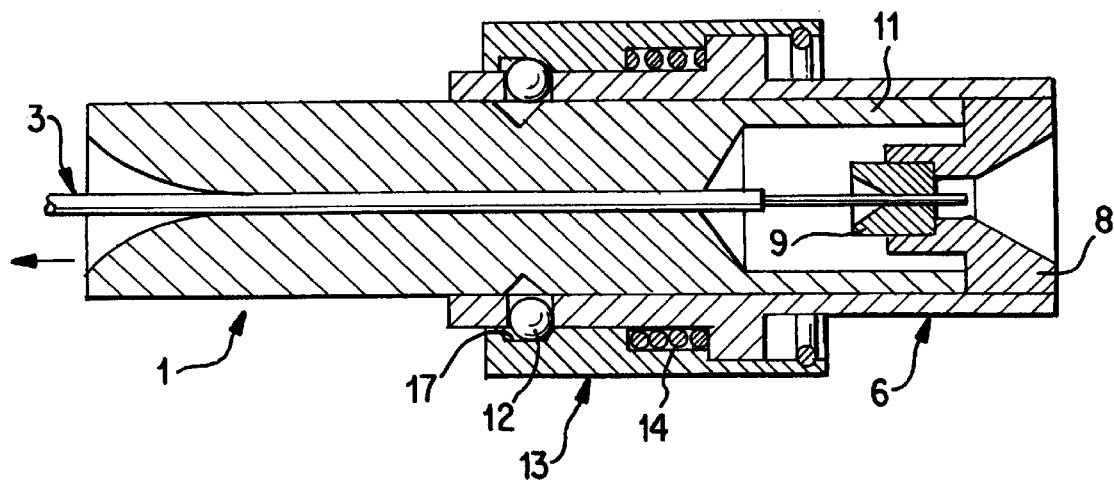
FIG. 2 is a sectional view corresponding to FIG. 1 of the coupling arrangement in the unlatched position.

FIGS. 1 and 2 show a fiber plug 1 which is fastened on the elastic fiber cladding 2 of an optical waveguide 3 by shrinking-on, chucking, gluing, or injection molding. The front end 4 of the optical waveguide, which is bared down to the optical fiber cladding of the optical waveguide 5, projects freely toward the front. The fiber plug 1 is used for the plugging into a countercoupling part 6 which, in the embodiment according to FIGS. 1 and 2, represents the output jack of a laser, in which case the optical axis 7 of the laser beam is aligned precisely with respect to a centering unit 8 with a centering sleeve 9. When the fiber plug 1 is plugged together with the countercoupling part 6, the bared fiber 5 of the optical waveguide 3 is introduced into the centering sleeve through its introducing cone 10. In this case, the alignment of the optical waveguide fiber 5 with respect to the optical axis 7 is influenced only by the single tolerance between the outside diameter and the concentricity of the fiber 5 and the inside diameter of the centering sleeve 9. This tolerance, which must be kept extremely low, can be further reduced in that, as described in detail at the beginning, the centering sleeve 9 has an elastic diameter. As a result, an optical alignment of the optical waveguide fiber 5 is obtained with respect to the optical axis 7 of the laser which is completely independent of the other mechanical tolerances of the plug part and particularly of the tolerance of the connection of this fiber plug 1 with the countercoupling part 6. This means that the construction of the fiber plug 1 itself and its connection with the optical waveguide 3 can take place in a simple manner and without extreme precision and is therefore also suitable for a disposable article.

In the illustrated embodiment, the fiber plug 1 is constructed on the front end as a sleeve 11 surrounding the exposed bared fiber 5, which sleeve 11 is used as a plug-in stop on the centering unit 8. The releasable latching of the fiber plug 1 on the countercoupling part 6 takes place by a latching ball 12 which is pressed by a cap sleeve 13, which is under the effect of a pressure spring 14, into a ring groove 15, where it rests against the diagonal surface 16 in the latching position illustrated in FIG. 1. By the displacement of the cap sleeve 13 toward the right against the effect of the pressure spring 14, the latching ball 12 arrives in the recess 17 of the cap sleeve and therefore releases the fiber plug so that it can be pulled out of the countercoupling part 6.

Figure 3:
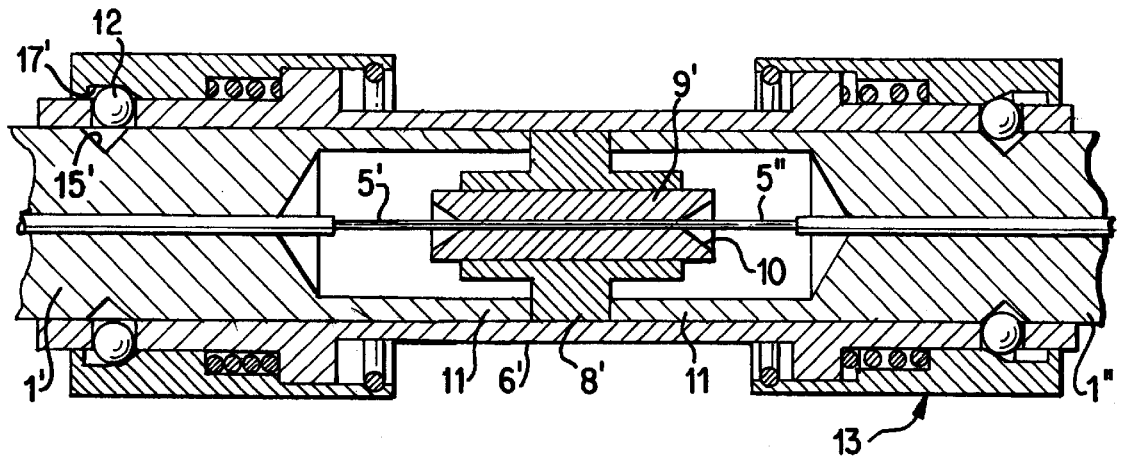
FIG. 3 is a sectional view of a coupling arrangement for connecting two optical waveguides having the fiber plugs constructed according to the invention.
Figure 4:
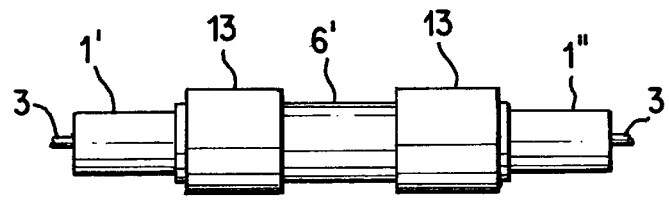
FIG. 4 is a lateral view of the coupling arrangement according to FIG. 3 in its original size.

FIGS. 3 and 4 show a coupling arrangement for connecting two optical waveguides which may be constructed as simple throw-away articles. In this case, the construction is basically the same as in FIG. 1, the centering unit 8', however, being situated in the center between two mutually aligned plug receiving devices for receiving the two fiber plugs 1' and 1".

It is therefore demonstrated that the construction according to the invention has the significant advantage with respect to all previous coupling arrangements that the mechanical components of the plug are used only as fastening and handling elements without being responsible for the precision of the optical coupling.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

I claim:

1. An arrangement for coupling an optical waveguide to an optical device comprising:

a fiber plug for holding said optical waveguide;

a countercoupling part of said optical device, with which said fiber plug can be connected; and a centering sleeve which is fixedly connected with the countercoupling part and aligned with the optical axis of the adjoining optical device; wherein an end of said waveguide is introduced into said countercoupling part and the fiber of said optical waveguide is introduced into said centering sleeve when said fiber plug is plugged into said countercoupling part;

said fiber plug is fastened on the elastic fiber cladding of said optical waveguide;

a freely projecting front end of said optical waveguide is bared down to the optical fiber cladding; and the bared fiber of the optical waveguide is introduced into said centering sleeve.

2. A coupling arrangement according to claim 1, wherein said centering sleeve is provided with an introducing cone.

3. a coupling arrangement according to claim 1, wherein said centering sleeve has an elastic diameter.

4. A coupling arrangement according to claim 1, wherein said fiber plug can be fastened on said countercoupling part by means of plug-in connections.

5. a coupling arrangement according to claim 1, wherein said fiber plug on a front end, surrounds the bared optical waveguide fiber at a distance as an insertion limiting sleeve.

6. A coupling arrangement according to claim 1, wherein said optical waveguide is couple to said fiber plug by one of gluing, clamping and shrink fitting.

7. A coupling arrangement according to claim 1, wherein said fiber plug is injection-molded onto said elastic fiber cladding of said optical waveguide.

* * * * *